United States Patent [19]

Ohata et al.

[11] 4,333,926

[45] Jun. 8, 1982

[54] STERYL-β-D-GLUCOSIDE PHARMACEUTICAL COMPOSITIONS AND USE

[75] Inventors: Katsuya Ohata; Tadatoshi Nomura; Masayoshi Watanabe, all of Kyoto, Japan

[73] Assignee: Nippon Shinyaku Co., Ltd., Kyoto, Japan

[21] Appl. No.: 42,048

[22] Filed: May 24, 1979

Related U.S. Application Data

[63] Continuation of Ser. No. 722,649, Sep. 13, 1976, abandoned, which is a continuation-in-part of Ser. No. 616,308, Sep. 24, 1975, abandoned, which is a continuation-in-part of Ser. No. 579,831, May 22, 1975, abandoned.

[51] Int. Cl.³ .................... A61K 31/70; A61K 31/705
[52] U.S. Cl. .................................................. 424/182
[58] Field of Search ............................. 424/180, 182

[56] References Cited

U.S. PATENT DOCUMENTS 2,415,313  2/1947  Thurman .......................... 424/180

OTHER PUBLICATIONS

Ma et al.—Arch. Biochem. Biophys., 1953, pp. 419–423.

Primary Examiner—Frederick E. Waddell
Attorney, Agent, or Firm—Jacobs & Jacobs

[57] ABSTRACT

Hemostatics, vascular stabilizers and anti-shock compositions containing at least one steryl-β-D-glucoside or monopalmitates thereof, of the formula:

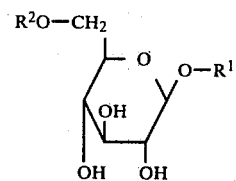

in which $R^1$ is β-sitosteryl, campesteryl, stigmasteryl or cholesteryl, and $R^2$ is hydrogen or palmitoyl. Methods of use are also described.

10 Claims, No Drawings

STERYL-β-D-GLUCOSIDE PHARMACEUTICAL COMPOSITIONS AND USE

CROSS-REFERENCE

This is a continuation of Ser. No. 722,649 filed Sept. 13, 1976, now abandoned, which in turn is a continuation-in-part of Ser. No. 616,308 filed Sept. 24, 1975 which in turn is a continuation-in-part of Ser. No. 579,831 filed May 22, 1975, both now abandoned.

DETAILED DESCRIPTION

It is known that natural plants have a styptic or hemostatic effect. Heretofore, it has been considered that such an effect was the result of components of the plants such as tannin, flavone and phosphatide. During a study of the compositions of these plant extracts, it was found that compounds of the following formula:

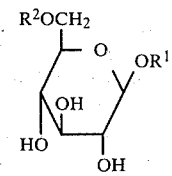

in which
$R^1$ is β-sitosteryl, campesteryl, stigmasteryl or cholesteryl, and
$R^2$ is hydrogen or palmitoyl,
are extremely effective styptic and hemostatic agents. Further study of these compounds has led to the finding that they also demonstrate phenomenal vascular stabilizing and antishock effects.

The present invention thus pertains to the use of these compounds in achieving hemostatic and vascular stabilization effects in animals, including humans, and to pharmaceutical compositions adapted for such use.

The compounds can be extracted from various kinds of natural plants or synthesized directly from β-sitosterol, campesterol, stigmasterol, cholesterol or mixtures thereof. When extracted from the plants, the compounds are generally obtained as mixtures of these sterols, primarily the first three. The ratio of these sterols will vary depending upon the plant from which the compounds are extracted, as can be seen from the following:

|  | β-sitosterol | Campesterol | Stigmasterol |
|---|---|---|---|
| Soybean | 56% | 21% | 23% |
| Cotton seed | 96 | 0 | 4 |
| Cicer arietinum | 87 | 3 | 10 |
| Grapefruit pulp | 84 | 7 | 9 |

The steryl-β-D-glucosides can be easily obtained from any of the above or similar plants by extraction, utilizing an organic solvent such as, for example, hexane, methanol, or acetone, optionally with hydrolysis of the extract, as for example, with caustic alkali or alkali carbonate. The following examples are representative of such methods.

EXAMPLE 1

Five hundred kilograms of well pulverized soybean are extracted with hexane and the lecithin component obtained by water treatment of the hexane solution is separated, combined with 2 liters of methanol and 200 g. of potassium hydroxide, and heated at reflux for 4 hours. Thereafter, the mixture is further diluted with 8 liters of aqueous methanol and allowed to stand until crystals separate. These crystals are collected by filtration and recrystallized from methanol. There is thus obtained 20 g. of colorless crystals melting from 300° to 310° C. (dec.), and which are soluble in pyridine and dioxane but insoluble in other organic solvents and water.

EXAMPLE 2

A mixture of 2.9 g. of cholesterol, 4.1 g. of α-acetobromoglucose, and small amounts of calcium hydride and silver oxide are added to 60 ml of anhydrous ether. The mixture is agitated at room temperature for 7.5 hours. The solvent is then removed by distillation and the residue is purified by silica gel chromatography. The purified substance is recrystallized from ethanol to yield 2.1 g. of crystalline cholesteryl-2,3,4,6-tetra-0-acetyl-β-D-glucopyranoside, m.p. 162° to 163° C. This compound is dissolved in 200 ml of ammoniacal methanol and the solution is allowed to stand for 20 hours. Water is then added and the resultant crystals are collected and recrystallized from ethanol to obtain 1.0 g. of crystalline product melting from 300° to 310° C. (dec.). The physico-chemical properties of the material are the same as those of the material obtained in Example 1.

EXAMPLE 3

The process of Example 2 is followed by using 1 g. of campesterol, 1.3 g. of α-acetobromoglucose, 0.7 g. of calcium hydride, 0.2 g. of silver oxide in 600 ml of ether to yield 0.3 g. of the desired campesteryl compound. This compound has a melting point of 300° C. (dec.) and properties similar to those of the material obtained in Example 1.

EXAMPLE 4

A mixture of 165.7 g. of the steryl-β-D-glucoside obtained in Example 1, 312 g. of methyl palmitate, 40 g. of potassium carbonate and 1.2 liter of N,N-dimethylformamide is agitated with heating at 120° C. During the reaction, the pressure is reduced for a period of 5 minutes every 2 hours and the produced methanol is removed by distillation. After 20 hours of reaction, the remaining solvent is also removed by distillation. The residue is taken up with 1 liter of benzene and cooled, and the resultant crystals are collected by filtration. A benzene solution of the separated crystals is then passed through a silica gel column and the resultant material is recrystallized from ethanol to yield 46 g. of colorless crystals, having a m.p. of 198°–200° C. and easily soluble in non-polar organic solvents such as benzene but only sparingly soluble in water.

The physico-chemical properties of the steryl-β-D-glucosides and their 6-monopalmitates can be summarized as follows:

|  | Melting Point |
|---|---|
| β-sitosteryl-β-D-glucoside | 300–310° C. (dec.) |
| Campesteryl-β-D-glucoside | 300° C. (dec.) |
| Stigmasteryl-β-D-glucoside | 300–310° C. (dec.) |
| Cholesteryl-β-D-glucoside | 300–310° C. (dec.) |
| β-sitosteryl-β-D-glucoside-6-monopalmitate | 198–200° C. |
| Campesteryl-β-D-glucoside-6-monopalmitate | 197–199° C. |
| Stigmasteryl-β-D-glucoside-6-monopalmitate | 198–200° C. |

-continued

| | Melting Point |
|---|---|
| Cholesteryl-$\beta$-D-glucoside-6-monopalmitate | 198–200° C. |

The pharmacological properties of these compounds, which are all similar to one another and hence substantially equivalent regardless of the ratio in which they are mixed, can be conveniently demonstrated in recognized laboratory models. For example, the following tables summarize the vascular stabilizing effect (described in detail below).

| Compound | Vascular stability (i.v.) ED$_{50}$ (mg/kg) |
|---|---|
| $\beta$-sitosteryl-$\beta$-D-glucoside | 1.48 |
| Campesteryl-$\beta$-D-glucoside | 2.40 |
| Stigmasteryl-$\beta$-D-glucoside | 2.33 |
| Cholesteryl-$\beta$-D-glucoside | 1.80 |
| Soybean steryl-$\beta$-D-glucoside | 2.00 |
| Cotton seed steryl-$\beta$-D-glucoside | 2.30 |
| Cicer arietinum steryl-$\beta$-D-glucoside | 1.65 |
| Grapefruit steryl-$\beta$-D-glucoside | 2.18 |
| Soybean steryl-$\beta$-D-glucoside-6-monopalmitate | 3.23 |

The acute toxicity (LD$_{50}$) of steryl-$\beta$-D-glucoside-monopalmitate in male mice was calculated according to the Litchfield-Wilcoxon method and can be summarized as follows:

| Compound | LD$_{50}$ (mg/kg) | | |
|---|---|---|---|
| | i.v. | i.p. | p.o. |
| Steryl-$\beta$-D-glucoside | >8 | 2770 | >3000 |
| Steryl-$\beta$-D-glucoside monopalmitate | >40 | >3000 | >3000 |

The hemostatic effect of steryl-$\beta$-D-glucoside (GS) and steryl-glucoside-monopalmitate (GSP) can be observed in the Motohashi et al. model [Tokyo Jikeikai Medical College Bulletin 75 (5) 1959] by sharply amputating 1 cm-long tail tip of each of the mice divided in groups of ten and measuring the time which elapsed until threadlike bleeding from the amputated tail end in water is completely stopped. The results, together with analogous results for known hemostatic agents, can be summarized as follows:

TABLE 1

| Compound | ED$_{50}$ (mg/kg) | | |
|---|---|---|---|
| | i.v. | i.p. | p.o. |
| SG | 0.082 | 0.110 | 1.66 |
| SGP | 0.100 | 0.140 | 2.88 |
| Carbazochrome sodium sulfonate (Adona AC-17) | 3.6 | 5.4 | 36.0 |
| Conjugated estrogen (Premalin) | 14.5 | — | — |

As is apparent from the above, SG was approximately 45 times as effective on i.v. and i.p. administrations and approximately 22 times as effective on p.o. administration as the control drug carbazochrome sodium sulfonate and about 177 times as effective on i.v. administration as conjugated estrogen (ref. lit.: Wallner et al. Med. Klin. 66 1413, 1971). SGP was approximately 37 times as effective on i.v. and i.p. administrations and approximately 12 times as effective on p.o. administration as carbazochrome sodium sulfonate and approximately 145 times as effective on i.v. administration as conjugated estrogen.

The hemostatic effect can also be observed by measuring the inhibitory effect on bleeding from ear vein in rabbits. The duration of bleeding after puncture of ear veins of rabbits is thus measured, noting the time of bleeding from rabbit punctured ear veins three hours after administration of each test compound, and expressing the time reduction rate against the time of bleeding from non-treated animals, according to the method of Duke, J.A.M.A., 1185, 1950.

TABLE 2

| Compound | Dose (mg/kg) i.v. | % Reduction |
|---|---|---|
| SG | 0.1 | 41.2 |
| SGP | 0.1 | 28.6 |
| Carbazochrome sodium sulfonate | 10 | 20.0 |
| Conjugated estrogen | 10 | 22.8 |

It will be noted that SG and SGP produced more than a 100 fold higher hemostatic effect than carbazochrome sodium sulfonate or conjugated estrogen.

The effect of the compounds on hemorrhages induced by vesical mucosal resection in dogs can be shown by observing the inhibiting effect on bleeding (determined from the amount of blood pigments) in control dogs, according to the method of G. Dermaut et al., Arch. int. pharmacodyn, Vol. 146 517, 1963.

TABLE 3

| Compound | Dose (mg/kg) i.v. | % Inhibition |
|---|---|---|
| SG | 0.1 | 47.9 |
| SGP | 0.4 | 38.1 |
| Carbazochrome sodium sulfonate | 5 | 39.9 |
| Conjugated estrogen | 10 | 48.6 |

Again it will be seen that SG has about 50 times as high a hemorrhage inhibitory effect as carbazochrome sodium sulfonate and 100 times as high an effect as conjugated estrogen, while SGP has shown 12.5 times and 25 times as high a hemorrhage inhibitory effect as carbazochrome sodium sulfonate and conjugated estrogen, respectively.

This inhibitory effect can also be seen on gastric mucosal hemorrhaging induced by electroshock in rats. The dosage of each test drug required for inhibiting gastric mucosal hemorrhage induced by electroshock (100–200 V, 3 times/min., 24 hours) in 50% of the rats (ED$_{50}$) was calculated according to the method of T. Danno et al., J. Pharm. Soc. of Japan, Vol. 80 1476 1960.

TABLE 4

| Compound | ED$_{50}$ (mg/kg, s.c.) |
|---|---|
| SG | 20.0 |
| SGP | 66.0 |
| Carbazochrome sodium sulfonate | >200.0 |
| Conjugated estrogen | >50.0 |

SG and SGP showed prominent electroshock hemorrhage arresting effect with ED$_{50s}$ of 20 mg/kg and 66 mg/kg, respectively, but no noticeable effect was produced by a dose of 200 mg/kg of carbazochrome sodium sulfonate nor by a dose of 50 mg/kg of conjugated estrogen.

The inhibitory effect of SG and SGP on local hemorrhage induced by abdominal intracutaneous administration of snake venom (Naja Naja cobra) in rats was determined in terms of inhibiting rate against untreated control rats.

TABLE 5

| Compound | Dose (mg/kg) i.p. | % Inhibition |
|---|---|---|
| SG | 20 | 35.0 |
| SGP | 40 | 45.0 |
| Carbazochrome sodium sulfonate | 100 | 9.1 |
| Conjugated estrogen | 50 | 11.0 |

Against the strong hemorrhagic action of this snake venom, SG showed an inhibitory effect of 35% at 20 mg/kg while SGP showed a 45% inhibitory effect at 40 mg/kg. Carbazochrome sodium sulfonate and conjugated estrogen showed only slight effects at 100 mg/kg and 50 mg/kg, respectively.

The surprising vascular stabilizing effect of these compounds can also be shown in a number of recognized models of which the following are typical.

The degree of pulmonary homorrhage in mice under reduced pressure of 50±0.5 mm Hg/15 sec was assessed by the scoring method, the $ED_{50}$ of each compound being calculated from the ratio of inhibiting rate for treated animals over that for the control group according to the method of G. J. Mojovski et al., J. Pharmacol. Exp. Therap. 80, 1, 1944.

TABLE 6

| Compound | $ED_{50}$ (mg/kg) | | |
|---|---|---|---|
| | i.v. | i.p. | p.o. |
| SG | 2.00 | 1.70 | 58.0 |
| SGP | 3.23 | 5.50 | 42.2 |
| Carbazochrome sodium sulfonate | 80.0 | 112.0 | 400.0 |
| Conjugated estrogen | — | 100.0 | — |

SG was more than 40 times more effective on i.v. administration, approximately 55 times more effective on i.p. administration and more than 7 times more effective on p.o. administration than carbazochrome sodium sulfonate and more than 50 times more effective on i.p. administration than conjugated estrogen. SGP was more than 25 times more effective on i.v. administration, about 20 times more effective on i.p. administration and more than 9.5 times more effective on p.o. administration than carbazochrome sodium sulfonate and about 19 times more effective on i.v. administration than conjugated estrogen.

The effect on abdominal cutaneous vascular resistance in guinea-pigs can also be used as a model of vascular stabilization. The time of appearance of petechia in abdominal skin of guinea-pigs under reduced pressure of 250 to 260 mm Hg is used as the index, with the petechia appearance delaying effect of each test compound in comparison with the control being determined according to the method of V. Borbely et al., Münch. Med. W. 77, 886, 1930.

TABLE 7

| Compound | Dose (mg/kg, s.c.) | Prolongation Rate (test group/control group) |
|---|---|---|
| SG | 10 | 2.5 |
| Carbazochrome sodium sulfonate | 100 | 1.7 |
| Conjugated estrogen | 100 | 1.9 |

SG is thus more than 10 times as potent in vascular resistance enhancing effects than carbazochrome sodium sulfonate or conjugated estrogen.

The inhibitory effect on increased vascular permeability caused by intracutaneous administration of histamine, hyaluronidase, lecithinase A and formalin is also correlated to vascular stabilization. This parameter was measured by the dye leakage method with the inhibitory effect of each test drug expressed in terms of inhibiting rate over the control according to the methods of Benditt et al., Proc. Soc. Biol. Med. 75 782 1950 and Orary et al., J. Exp. Med. 117, 951, 1963.

TABLE 8

| | Effect on increased vascular permeability caused by histamine | | |
|---|---|---|---|
| Compound | Dose (mg/kg, i.p.) | % Inhibition Rat | Rabbit |
| SG | 1 | 38.4 | 48.6 |
| SGP | 1 | 31.0 | 65.5 |
| Carbazochrome sodium sulfonate | 100 | 32.7 | 29.6 |
| Conjugated estrogen | 50 | 15.3 | 18.5 |

TABLE 9

| | Effect on increased vascular permeability induced by hyaluronidase | | |
|---|---|---|---|
| Compound | Dose (mg/kg, i.p.) | % Inhibition Rat | Rabbit |
| SG | 1 | 41.6 | 60.0 |
| SGP | 20 | 59.5 | 51.7 |
| Carbazochrome sodium sulfonate | 100 | −4.5 | 4.7 |
| Conjugated estrogen | 50 | −15.7 | 6.2 |

TABLE 10

| | Effect on increased vascular permeability in rabbits induced by lecithinase A | |
|---|---|---|
| Compound | Dose (mg/kg, i.p.) | % Inhibition |
| SG | 1 | 40.0 |
| SGP | 1 | 28.8 |
| Carbazochrome sodium sulfonate | 100 | 10.8 |
| Conjugated estrogen | 50 | 14.2 |

TABLE 11

| | Effect on increased vascular permeability in rabbits induced by formalin | |
|---|---|---|
| Compound | Dose (mg/kg, i.p.) | % Inhibition |
| SG | 1 | 42.9 |
| SGP | 1 | 52.3 |
| Carbazochrome sodium sulfonate | 100 | 0.4 |
| Conjugated estrogen | 50 | 0.8 |

The marked inhibitory effect of these compounds against increased vascular permeability induced by histamine, hyaluronidase, lecithinase A and formalin is thus apparent. This effect for SG is about 100 times greater than that of carbazochrome sodium sulfonate and about 50 times greater than that of conjugated estrogen. SGP similarly shows significant inhibitory effects on increased vascular permeability caused by histamine, lecithinase A and formalin, being about 100 times greater than that of carbazochrome sodium sulfonate and about 50 times greater than that of conjugated estrogen. For hyaluronidase, SGP is about 5 times more potent than carbazochrome sodium sulfonate and about 2.5 times more potent than conjugated estrogen at a dose of 20 mg/kg.

The compounds also show an inhibitory effect on the Arthus reaction in guinea-pigs. Increased vascular permeability five hours after provocation of reaction is measured as the leakage of hemoglobin according to the method of Benacerral et al., J. Immunol. Vol. 64 1–9, 1950. The effect of each compound in terms of inhibiting rate as against the control is shown in the following table.

TABLE 12

| Compound | Dose (mg/kg, i.p.) | % Inhibition |
| --- | --- | --- |
| SG | 1 | 64.0 |
| SGP | 10 | 33.8 |
| Carbazochrome sodium sulfonate | 100 | 26.3 |
| Conjugated estrogen | 50 | 31.2 |

SG is thus approximately 100 times as effective as carbazochrome sodium sulfonate and approximately 50 times as effective as conjugated estrogen, while SGP is 10 times as effective as carbazochrome sodium sulfonate and 5 times as effective as conjugated estrogen.

The anti-shock properties of these compounds can also be observed in recognized in vivo models.

The mortality rate during the period of 48 hours following intravenous administration of 80% lethal dose (8 mg/kg) of endotoxin is observed with the effect of each compound being expressed as the $ED_{50}$ (see Tanabe et al., Pharmacometrics Vol. 7 591, 1973).

TABLE 13

| Compound | Endotoxin Shock $ED_{50}$ (mg/kg, i.p.) |
| --- | --- |
| SG | 77.0 |
| SGP | 106.0 |
| Carbazochrome sodium sulfonate | >200.0 |
| Conjugated estrogen | >50.0 |

Both SG and SGP showed excellent inhibitory effect against death from strong endotoxin-shock and also markedly improved the shock symptoms of the survivors. Carbazochrome sodium sulfonate and conjugated estrogen were far inferior in effect to SG and SGP, and no niticeable effect was produced at the doses of less than 200 mg/kg and 50 mg/kg, respectively.

The preventive effect against passive systemic anaphylaxis was determined according to the method of Munoz et al., J. Immunol., 80, 77 (1958). An antigen of 80% lethal dose is intravenously administered to antiserum-sensitized guinea-pigs, and the resultant passive systemic anaphylaxis lethality is expressed as the inhibition rate as compared with the control group.

TABLE 14

| Compound | Dose (mg/kg, i.p.) | % Inhibition |
| --- | --- | --- |
| SG | 40 | 60 |
| SGP | 40 | 80 |
| Carbazochrome sodium sulfonate | 100 | 20 |
| Conjugated estrogen | 100 | 52 |

Both SG and SGP alleviate the symptoms of passive systemic anaphylaxis such as jumping and clonic convulsions and considerably reduce PSA fatality. On the other hand, carbazochrome sodium sulfonate shows only very slight effects at a dose of 100 mg/kg while conjugated estrogen shows an effect comparable with those of SG and SGP only at a dose two and a half times higher.

It is thus clear from the foregoing that steryl-$\beta$-D-glucoside and steryl-$\beta$-D-glucoside-monopalmitate produce excellent vascular stabilizing and antihemorrhagic effects at low doses. They are thus useful to arrest bleeding induced by various causes including wounds, postpartum hemorrhage, cerebral hemorrhage, surgical procedures and the like, and also specifically to act upon the vascular walls to produce a strengthening and protecting effect. Thus, these substances can be used as hemostatic agents which demonstrate low toxicity and are effective in arresting bleeding induced by various causes, as vascular strengthening agents for remedy or prevention of various vascular lesions, including peripheral vascular functional disorders caused by increased vascular permeability due to fragile blood vessels, and as anti-shock agents for various symptoms of shock.

The compounds of the present invention are administered parenterally, orally (including perlingually) rectally or topically in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

Typical parenteral formulations for injection are as follows:

Formulation A

| Ingredient | Amount |
|---|---|
| steryl-β-D-glucoside | 20 mg |
| NIKKOL HCO-60 polyoxyethylene (60)-hydrogenated castor oil | 1.2 g. |
| ethyl alcohol | 10 ml |
| glucose | 5 g |
| distilled water for injection | q.s. 100 ml |

This solution is divided into 20 ampoules, each ampoule containing 5 ml (corresponding to 1 mg of steryl-β-D-glucoside).

Formulation B

| Ingredient | Amount |
|---|---|
| steryl-β-D-glucoside-mono-palmitate | 100 mg |
| NIKKOL HCO-60 polyoxyethylene (60)-hydrogenated castor oil | 4 g. |
| ethyl alcohol | 5 ml |
| sodium chloride | 0.9 g. |
| distilled water for injection | q.s. 100 ml |

This solution is divided into 20 ampoules, each ampoule containing 5 ml (corresponding to 5 mg of steryl-β-D-glucoside monopalmitate).

For the purpose of reference and illustration, preferred dosages of injections (both intraperitoneal and intravascular) are as follows:

|  | Formulation A | Formulation B |
|---|---|---|
| Hemostatic purposes | 0.5–1 amp | — |
| Vascular stabilization | — | 1 amp |
| Anti-shock purposes | — | 2 amp |

The above dosages are given one or more times a day.

Typical powders to be administered as such or in capsules consist of the following:

| Ingredient | Amount Formulation A | Formulation B |
|---|---|---|
| steryl-β-D-glucoside | 1 g | 1 g |
| lactose | 99 g | 9 g |

Typical tablet compositions are as follows:

| Ingredient | Amount Formulation A | Formulation B |
|---|---|---|
| steryl-β-D-glucoside monopalmitate | 2.0 mg | 20 mg |
| lactose | 20.0 mg | 80 mg |
| starch | 7.8 mg | 49 mg |
| Avicel microcrystalline cellulose | 20.0 mg | 50 mg |
| magnesium stearate | 0.2 mg | 1 mg |

These are mixed and compressed as described above to form tablets.

Preferred daily dosages of capsules and tablets are as follows:

|  | Capsules Formulation A | B | Tablets Formulation A | B |
|---|---|---|---|---|
| Hemostatic purposes | 1–3 cap. | — | 1–3 tab. | — |
| Vascular stabilization | 3–10 cap. | — | 3–10 tab. | — |
| Anti-shock purposes | — | 3–10 cap. | — | 3–10 tab. |

The above dosages are taken preferably in two to four, more preferably three, times a day.

Typical formulations for rectal suppositories are as follows:

Formulation A

| | |
|---|---|
| Steryl-β-D-glucoside | 5 mg |
| WITEPSOL H-15 ointment base (Dynamit Nobel AG) | 1995 mg |

Formulation B

| | |
|---|---|
| Steryl-β-D-glucoside monopalmitate | 5 mg |
| WITEPSOL H-15 ointment base | 1495 mg |
| WITEPSOL S-55 ointment base | 500 mg |

One suppository of either Formulation A or Formulation B can be administered rectally 4 to 6 times a day.

Typical topical preparations are as follows:

Formulation A

Each ten (10) grams contains the following:

| | |
|---|---|
| Steryl-β-D-glucoside | 50 mg |
| Purified lanoline | 4900 mg |
| White petroleum jelly | 5050 mg |

Formulation B

Each ten (10) grams contains the following:

| Steryl-β-D-glucoside monopalmitate | 50 mg |
|---|---|
| Cetyl alcohol | 400 mg |
| Polyethyleneglycol 400 | 4980 mg |
| Polyethyleneglycol 4000 | 4570 mg |

Formulations A and B are applied topically to vascular lesions.

It will be appreciated that the administration of these compounds requires the exercise of sound professional judgment. In each case the dosage required to obtain a hemostatic and/or vascular protecting effect must be titrated to the patient, keeping in mind the age, condition, weight, response and effect desired.

What is claimed is:

1. The method of achieving hemostatic, vascular stabilization and anti-shock effect in humans and other animals in need thereof which comprises orally, parenterally, rectally or topically administering thereto an effective amount of at least one compound of the formula:

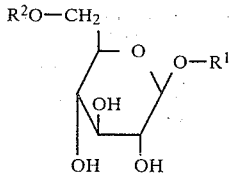

wherein
R$^1$ is β-sitosteryl, campesteryl, stigmasteryl or cholesteryl; and
R$^2$ is hydrogen or palmitoyl.

2. The method according to claim 1 wherein said compound is β-sitosteryl-β-D-glucoside.

3. The method according to claim 1 wherein said compound is campesteryl-β-D-glucoside.

4. The method according to claim 1 wherein said compound is stigmasteryl-β-D-glucoside.

5. The method according to claim 1 wherein said compound is cholesteryl-β-D-glucoside.

6. The method according to claim 1 wherein said compound is β-sitosteryl-β-D-glucoside-6-monopalmitate.

7. The method according to claim 1 wherein said compound is campesteryl-β-D-glucoside-6-monopalmitate.

8. The method according to claim 1 wherein said compound is stigmasteryl-β-D-glucoside-6-monopalmitate.

9. The method according to claim 1 wherein said compound is cholesteryl-β-D-glucoside-6-monopalmitate.

10. A solid pharmaceutical tablet or capsule in unit dosage form consisting essentially of at least one compound of the formula:

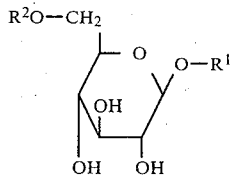

wherein
R$^1$ is β-sitosteryl, campesteryl, stigmasteryl or cholesteryl,
R$^2$ is hydrogen or palmitoyl, and a solid pharmaceutical carrier, said compound being present in said tablet or capsule in an amount calculated to produce, upon oral or perlingual administration to a human or other animal of one or more of said units, a hemostatic, vascular stabilization and anti-shock response.

* * * * *